US007731495B2

(12) United States Patent
Eisenberg et al.

(10) Patent No.: US 7,731,495 B2
(45) Date of Patent: Jun. 8, 2010

(54) USER INTERFACE HAVING CROSS SECTION CONTROL TOOL FOR DIGITAL ORTHODONTICS

(75) Inventors: Peter M. Eisenberg, Minneapolis, MN (US); Nicholas A. Stark, Cottage Grove, MN (US); Richard E. Raby, North St. Paul, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 475 days.

(21) Appl. No.: 11/275,236

(22) Filed: Dec. 20, 2005

(65) Prior Publication Data

US 2007/0141526 A1 Jun. 21, 2007

(51) Int. Cl.
*A61C 3/00* (2006.01)
*G06F 3/048* (2006.01)

(52) U.S. Cl. ......................... 433/24; 715/848
(58) Field of Classification Search .................. 433/24; 715/848, 964
See application file for complete search history.

(56) References Cited

U.S. PATENT DOCUMENTS

| 5,623,583 | A  | * | 4/1997  | Nishino ..................... 345/420 |
| 6,664,986 | B1 |   | 12/2003 | Kopelman et al. |
| 6,898,302 | B1 |   | 5/2005  | Brummer |
| 6,976,840 | B2 |   | 12/2005 | Taub et al. |
| 7,033,327 | B2 |   | 4/2006  | Raby |
| 2002/0010568 | A1 | * | 1/2002 | Rubbert et al. ................. 703/6 |
| 2002/0015006 | A1 | * | 2/2002 | Suzuki et al. ................... 345/6 |
| 2002/0025503 | A1 | * | 2/2002 | Chapoulaud et al. ........... 433/24 |
| 2003/0215764 | A1 | * | 11/2003 | Kopelman et al. ............. 433/24 |
| 2004/0096799 | A1 | * | 5/2004 | Hughes et al. ................. 433/24 |
| 2004/0175670 | A1 |   | 9/2004  | Kopelman et al. |
| 2004/0197727 | A1 |   | 10/2004 | Sachdeva et al. |
| 2005/0033160 | A1 | * | 2/2005 | Yamagata et al. ........... 600/425 |
| 2005/0130095 | A1 |   | 6/2005  | Raby et al. |
| 2005/0170309 | A1 |   | 8/2005  | Raby et al. |
| 2005/0214707 | A1 |   | 9/2005  | Kohani |
| 2006/0024637 | A1 |   | 2/2006  | Raby et al. |
| 2006/0073436 | A1 |   | 4/2006  | Raby et al. |

FOREIGN PATENT DOCUMENTS

WO    WO 98/53428    11/1998

OTHER PUBLICATIONS

Visualization in biomedical computing, Richard A. Robb, Parallel Computing 25 (1999) 2067-2110.
Anatomy Browser: A novel approach to visualization and integration of medical information; Goliand et al., Computer Assisted Surgery, 4:129-143, 1999.
User Controlled Overviews of an Image Library: A Case Study of the Visible Human; North et al., Human-Computer Interaction Laboratory, Department of Computer Science, Institute for Systems Research, University of Maryland, 1996, pp. 74-82.

* cited by examiner

*Primary Examiner*—Cris L Rodriguez
*Assistant Examiner*—Heidi M Eide

(57) ABSTRACT

Techniques are described for providing an environment to model and depict a three-dimensional (3D) representation of a patient's dental arch, i.e., a virtual dental arch, and a separate cross section tool, such as a graphical user interface (GUI), as a visual aid to an orthodontic practitioner for selecting a position of cross section planes relative to the virtual dental arch. The GUI may display a control image and two moveable parallel lines. The position of the parallel lines relative to the control image approximates the position of the cross section planes relative to the virtual dental arch. Thus, by interacting with the GUI, the practitioner is able to change the position of the cross section planes within the 3D environment. Consequently, the practitioner can visualize the cross sections of the virtual dental arch within the 3D environment while selecting the position of the cross section planes.

18 Claims, 9 Drawing Sheets

USER INTERFACE HAVING CROSS SECTION CONTROL TOOL FOR DIGITAL ORTHODONTICS

TECHNICAL FIELD

The invention relates to electronic orthodontics and, more particularly, computer-implemented techniques for assisting orthodontic diagnosis and treatment.

BACKGROUND

The field of orthodontics is concerned with repositioning and aligning a patient's teeth for improved occlusion and aesthetic appearance. The state of the art in orthodontics is moving toward digital and computer-aided techniques. These techniques include the use of intra and extra-oral scanners, three-dimensional (3D) modeling of a patient's tooth structure, and fabrication of orthodontic devices from digital data.

For example, a scanner is used to capture three-dimensional (3D) data associated with a patient's teeth, and a computer system renders a graphical representation of the patient's teeth or dental arch based on the captured data. The computer system provides an environment for modeling and depicting a 3D representation or virtual model of the patient's dental arch, and aids the orthodontic practitioner in rendering an orthodontic diagnosis.

SUMMARY

In general, the invention relates to techniques for assisting orthodontic practitioners in orthodontic diagnosis and treatment. For example, a system is described that provides an environment for modeling and depicting a three-dimensional (3D) digital representation of a patient's dental arch. The system provides a graphical user interface (GUI) that presents a separate cross section control as a visual aid to an orthodontic practitioner for selecting a position of one or more cross section planes within the 3D environment relative to the digital representation of the dental arch. By interacting with the GUI, the practitioners are able to change the position of the cross section planes in the 3D environment, thereby changing attributes, e.g., location and orientation, of cross sections of the patient's dental arch rendered by the system.

As one example, in addition to rendering at least a portion of a patient's virtual dental arch, the GUI may display a second representation of a dental arch for use as a control image. By positioning one or more cross section controls (e.g., parallel lines) relative to the control image, a practitioner may define the position and overall width of the cross section of the patient's virtual dental arch rendered by the system. The cross section planes may be displayed as semi-transparent two-dimensional (2D) planes within the 3D environment and define the cross section of the virtual dental arch. The position of the cross section controls relative to the control image defines the position of the cross section planes relative to the patient's virtual dental arch, and the intersection of the cross section planes with the patient's virtual dental arch defines the cross section area of the virtual dental arch to be rendered.

The 3D environment may include controls that allow the practitioner to view the virtual dental arch from various viewpoints, e.g., by rotating or tilting the virtual dental arch within the 3D environment. Typically, it is useful for the practitioner to view the cross section area of the virtual dental arch while changing the position of the cross section planes. In this case, however, the cross section area is parallel to the viewing plane in conventional systems. Thus, adjusting the position of the cross section planes relative to the virtual dental arch, i.e., moving the cross section plane toward or away from the viewing plane, using controls in the 3D environment may not be intuitive to the practitioner or may not even be possible at all.

The GUI of the present system may display the control image as a plan view image of a dental arch orthogonal to the cross section planes in the 3D environment and one or more cross section controls (e.g., two moveable parallel lines) for selecting the position of the cross section planes. In particular, the GUI may display a plan view image of a generic dental arch, such as an icon or background image, or a scaled (e.g., low resolution) plan view image of the patient's virtual dental arch. The practitioner may select the positions of the parallel lines using, for example, a mouse, joystick, keyboard, or other input device. For example, the practitioner may adjust the location of the parallel lines by moving horizontal lines up and down or vertical lines side to side relative to the control image to set the limits of the cross section. The practitioner may also adjust the orientation of the parallel lines, i.e., rotate the parallel lines relative to the horizontal or vertical axis.

As the practitioner selects the position of the parallel lines relative to the control image of the dental arch within the GUI, the system automatically adjusts the cross section planes relative to the patient's virtual dental arch within the 3D environment to display the appropriate cross section. When the practitioner has selected the desired cross section, the practitioner may manipulate the virtual dental arch using controls associated with the 3D environment to view the virtual dental arch from various viewpoints. For example, the practitioner may rotate or tilt the virtual dental arch back and forth within the 3D environment to compare cross section areas located on opposite sides of the virtual dental arch. Advantageously, the GUI may manipulate the display of the patient's virtual dental arch without modifying the display of the control image. In this manner, the control image within the GUI only serves to provide a visual aid for selecting the position of the cross section planes and to convey the type of cross section being manipulated.

In addition, as the practitioner positions the parallel lines, the system also may automatically adjust the plan view image of the dental arch within the GUI to better show the selected cross section area. For example, the system may shade the portion of the control image that is to be excised from the rendering of the patient's dental arch or may not display the excised portion at all. Consequently, the control image represents the changing cross section of the patient's virtual dental arch within the 3D environment as the practitioner uses the GUI as a visual aid to change the position of one or more cross section planes relative to the virtual dental arch by manipulating the cross section control relative to the control image.

In one embodiment, the invention is directed to a method comprising displaying a graphical user interface (GUI) having a first region that displays a representation of at least a portion of a patient's dental arch within a three-dimensional (3D) environment and a second region that displays a representation of a second dental arch and at least one cross section control for selecting a position of at least one cross section plane relative to the patient's dental arch, and rendering a cross section of the patient's dental arch based on the selected position of the cross section plane.

In another embodiment, the invention is directed to a system comprising a computing device, and three-dimensional (3D) modeling software executing on the computing device, wherein the modeling software comprises a graphical user interface (GUI) that displays a digital representation of a cross section of a patient's dental arch, a second dental arch and a cross section control positionable relative to the second dental arch, and a rendering engine that renders the cross section of the patient's dental arch based on a selected position of the cross section control relative to the second dental arch.

In another embodiment, the invention is directed to a computer-readable medium containing instructions. The instructions cause a programmable processor to display a graphical user interface (GUI) having a control image and a cross section control movable by a practitioner for selecting a position of at least one cross section plane relative to a digital representation of a dental arch within a separate three-dimensional (3D) environment, and render the digital representation of the dental arch within the 3D environment based on the selected positions of the cross section plane.

The details of one or more embodiments of the invention are set forth in the accompanying drawings and the description below. Other features, objects, and advantages of the invention will be apparent from the description and drawings, and from the claims.

One benefit of this system is that it keeps a statically oriented view showing the current cross section which can be used as a reference by the practitioner—many of the possible 3D views can be disorienting and make it hard to interpret the exact nature/location of the current cross section. In this manner, the GUI provides a clear indication of the type of cross section being shown and a relative idea of the extent of the cross section.

DETAILED DESCRIPTION

Figure 1:
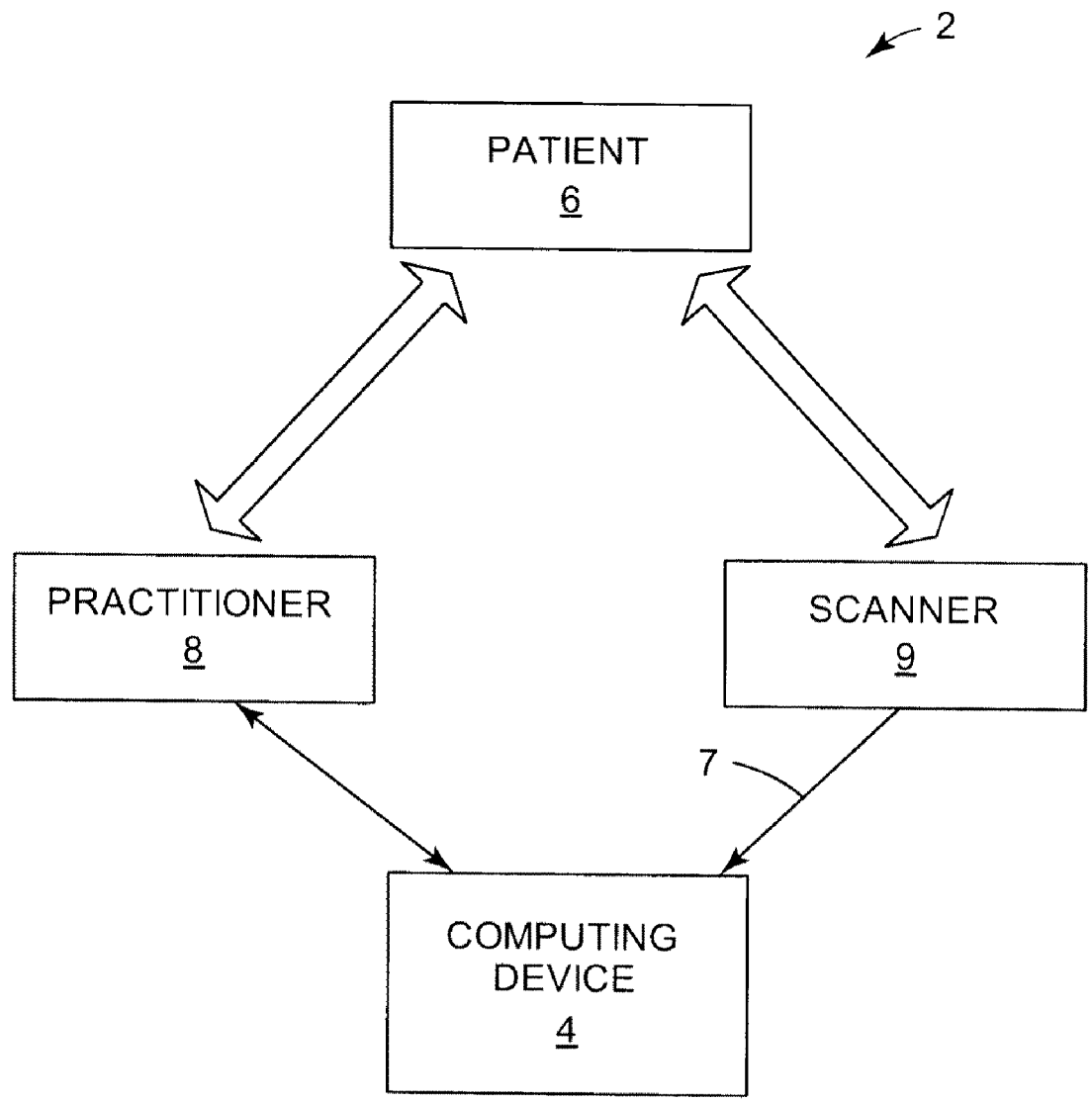
FIG. 1 is a block diagram illustrating an exemplary computer environment in which a client computing device presents a three-dimensional (3D) environment for visualizing a digital representation of a patient's dental arch and a separate representation of a dental arch as a visual aid for selecting a cross section of the patient's dental arch within the 3D environment.

FIG. 1 is a block diagram illustrating an exemplary computer environment 2 in which a computing device 4 presents an environment for modeling and depicting a three-dimensional (3D) digital representation of a dental arch of patient 6. The 3D digital representation of the patient's dental arch, i.e., "the virtual dental arch," may be initially generated from digital data 7 generated by digitally scanning a physical dental impression or other model of the teeth of patient 6 with scanner 9. Alternatively, practitioner 8 may use an intraoral scanner to produce digital data 7 directly from the teeth of patient 6.

The 3D modeling environment provided by computing device 4 models and renders a 3D representation or virtual model of the patient's dental arch, and aids the orthodontic practitioner 8 in rendering an orthodontic diagnosis. For appropriate orthodontic diagnostics, orthodontic practitioner 8 analyzes the virtual model of the dental arch of patient 6 from various viewpoints. In certain embodiments, orthodontic practitioner 8 utilizes the 3D modeling environment for treatment planning by viewing the virtual model of the patient's dental arch in a malocclusion state and in a predicted final occlusion state computed by device 4. In the final occlusion state, the efficacy of the treatment plan, including the choice of orthodontic appliances and their positions on the teeth, may be determined, in part, by viewing cross-sections of the patient's tooth structure (e.g., one or more arches) posed in a predicted final occlusion. As one example, computing device 4 allows practitioner 8 to view cross-sections of maxillary and mandibular arches set in predicted maximum intercuspation. Such cross-sectional views may reveal interferences between antagonist teeth (i.e., opposing maxillary and mandibular teeth) or adjacent teeth.

As described herein, computing device 4 provides a graphical user interface that presents a virtual representation of the patient's dental arch. In addition, the GUI presents a separate cross section tool for selecting position of one or more cross section planes relative to the dental arch within the 3D environment. By interacting with the GUI, practitioner 8 is able to change the positions of the cross section planes in the 3D environment, thereby changing attributes, e.g., location and orientation, of cross sections of the patient's dental arch rendered by the computing device 4.

In general, practitioner 8 interacts with the modeling software to view the virtual dental arch and, more particularly, a cross section area of the virtual dental arch from various views. In addition to rendering at least a portion of a patient's virtual dental arch, computing device 4 displays a second representation of a dental arch for use as a control image. By positioning one or more cross section controls (e.g., parallel lines) relative to the control image, practitioner 8 may define the position and overall width of the cross section of the patient's virtual dental arch rendered by the computing device 4. The cross section planes may be displayed as semi-transparent two-dimensional (2D) planes within the 3D environment and define the cross section of the virtual dental arch. The position of the cross section controls relative to the control image defines the position of the cross section planes relative to the patient's virtual dental arch, and the intersection of the cross section planes with the patient's virtual dental arch defines the cross section area of the virtual dental arch to be rendered.

The 3D environment provided by computing device 4 may include controls that allow the practitioner to view the virtual dental arch from various viewpoints, e.g., by rotating or tilting the virtual dental arch within the 3D environment. The GUI presented by computing device 4 may display the control image as a plan view image of a dental arch orthogonal to the cross section planes in the 3D environment, and may display one or more cross section controls (e.g., two moveable parallel lines) proximate to the control image for selecting the position of the cross section planes. In one embodiment, the GUI of computing device 4 displays the control image as a plan view image of a generic dental arch, such as an icon or background image. In another embodiment, the GUI presents the control image as a scaled (e.g., low resolution) plan view image of the patient's virtual dental arch. Practitioner 6 may select the positions of the parallel lines using, for example, a mouse, joystick, keyboard, or other input device. For example, practitioner 6 may adjust the location of the parallel lines by moving horizontal lines up and down or vertical lines side to side relative to the control image to set the limits of the cross section. The practitioner may also adjust the orientation of the parallel lines, i.e., rotate the parallel lines relative to the horizontal or vertical axis.

As the practitioner selects the position of the parallel lines relative to the control image of the dental arch within the GUI, the system automatically adjusts the cross section planes relative to the patient's virtual dental arch within the 3D environment to display the appropriate cross section. When the practitioner has selected the desired cross section, the practitioner may manipulate the virtual dental arch using controls associated with the 3D environment to view the virtual dental arch from various viewpoints. For example, the practitioner may rotate or tilt the virtual dental arch back and forth within the 3D environment to compare cross section areas located on opposite sides of the virtual dental arch. Advantageously, the GUI may manipulate the display of the patient's virtual dental arch without modifying the display of the control image. In this manner, the control image within the GUI only serves to provide a visual aid for selecting the position of the cross section planes and to convey the type of cross section being manipulated.

In addition, as the practitioner positions the parallel lines, the system also may automatically adjust the plan view image of the dental arch within the GUI to better show the selected cross section area. For example, the system may shade the portion of the control image that is to be excised from the rendering of the patient's dental arch or may not display the excised portion at all. Consequently, the control image represents the changing cross section of the patient's virtual dental arch within the 3D environment as the practitioner uses the GUI as a visual aid to change the position of one or more cross section planes relative to the virtual dental arch by manipulating the cross section control relative to the control image.

In some embodiments, the control image may comprise an icon or background image of a plan view image of a generic dental arch. In other embodiments, the control image may comprise a scaled image (e.g., a low resolution version) of the virtual dental arch of the patient 6. In any case, the modeling software executing on computing device 4 generates the GUI based on the type of cross section selected by practitioner 8. For example, when practitioner 8 selects a frontal cross section, the modeling software may generate a front plan view image of a generic dental arch and two vertical moveable parallel lines. When practitioner 8 selects a sagittal cross section, the modeling software may generate a side plan view image (also known as a lateral view or a buccal view) of a generic dental arch and two vertical moveable parallel lines. When practitioner 8 selects an occlusal cross section, the modeling software may generate a front plan view of a generic dental arch and two horizontal moveable parallel lines.

Once practitioner 8 has selected the type of cross section, practitioner 8 may select the position of the moveable parallel lines. For example, practitioner 8 may select the position of the moveable parallel lines using a mouse, joystick, keyboard, or other input device. In addition to selecting the position of the moveable parallel lines by moving vertical lines side-to-side and horizontal lines up-and-down, practitioner 8 may also rotate or adjust the orientation of the parallel lines. For example, the end points of the parallel lines may change to a rotation icon when a cursor is positioned over any of the end points, thereby allowing practitioner 8 to manipulate the orientation of the parallel lines by manipulating the pointing device.

The modeling software executing on computing device 4 automatically adjusts the virtual dental arch within the 3D environment as practitioner 8 adjusts the position and orientation of the parallel lines relative to the control image within the GUI. For example, the modeling software automatically adjusts the position of the cross section planes within the 3D environment as practitioner 8 adjusts the position of the parallel lines within the GUI. Thus, practitioner 8 can view the cross section area of the virtual dental arch while adjusting the position of the cross section planes by moving the parallel lines within the GUI relative to the control image.

Consequently, computing device 4 may assist practitioner 8 in visualizing any portion of the virtual dental arch that may be penetrating the cross section plane. As an example, practitioner 8 may use client computing device to assist in determining which occlusal edges of the virtual dental arch penetrate an occlusal plane first. In another example, the ability to rotate or bias the cross section planes may be useful in situations where practitioner wants to align the cross section along the mid-frontal, mid-sagittal, or mid-lateral plane of a tooth but the tooth is rotated in its socket so the plane is not parallel to a vertical or horizontal axis of the 3D environment.

The GUI may also automatically adjust the control image as practitioner 8 adjusts the positions of the parallel lines to better show the selected cross section. For example, modeling software may represent the portion of the control image that is not located between the parallel lines, i.e., the not-in-view portion of the control image, as a shaded-out portion or may not display the not-in-view portion at all. In this manner, the GUI provides a clear indication of the type of cross section being shown and a relative idea of the extent of the cross section.

Once practitioner 8 has selected a desired cross section, practitioner 8 may view the virtual dental arch from various view points by interacting with controls associated with the 3D environment. For example, practitioner 8 may rotate the virtual dental arch back and forth to compare opposite sides of the cross section. Moreover, the modeling software allows the practitioner to manipulate the virtual dental arch of patient 6 without necessarily changing the view of the control image within the GUI, i.e., the orientation of the control image is constant regardless of the orientation of the virtual dental arch. As such, the control image and the cross section controls are always visible and accessible for easy manipulation regardless of the orientation of the virtual dental arch within the 3D environment. In this manner, the invention provides an intuitive interface for selecting the position of cross section planes and, thus, viewing the cross section area of a virtual dental arch while easily adjusting the cross section planes.

Figure 2:
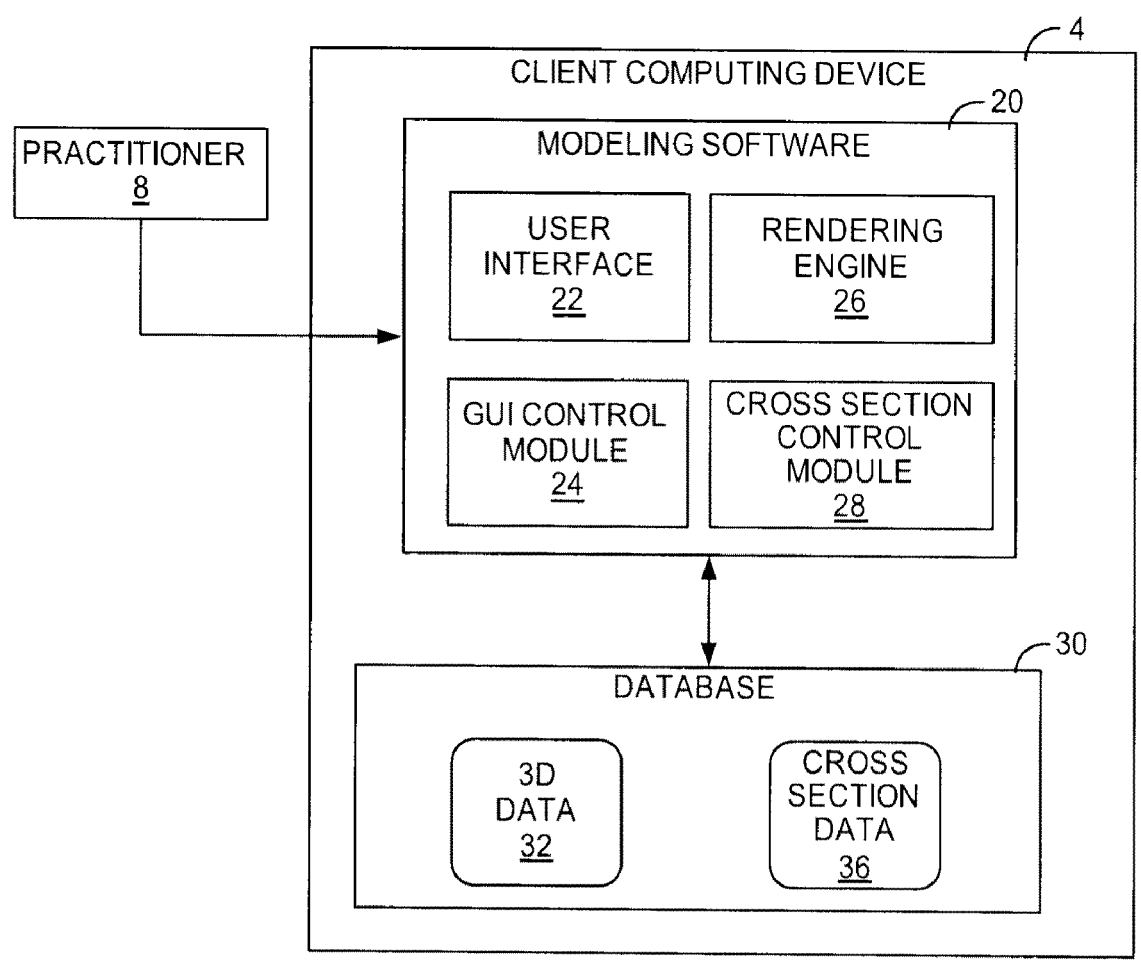
FIG. 2 is a block diagram illustrating an example embodiment of the client computing device of FIG. 1 in further detail

FIG. 2 is a block diagram illustrating an example embodiment of computing device 4 in further detail. In the illustrated embodiment, computing device 4 provides an operating environment for modeling software 20. As described above, modeling software 20 presents a modeling environment for modeling and depicting the 3D representation or virtual dental arch of the teeth of patient 6 and a separate cross section tool for selecting the position of cross section planes relative to the dental arch within the 3D environment. In the illustrated embodiment, modeling software 20 includes a user interface 22, a GUI control module 24, a rendering engine 26, and a cross section control module 28.

User interface 22 provides the 3D modeling environment that visually displays the 3D representation or virtual dental arch of the patient's teeth, and optionally displays one or more cross section planes. For example, the 3D environment may comprise a window in which the virtual dental and cross section planes are displayed. In one embodiment, user interface 22 displays two cross section planes which are positioned to limit the overall width of the cross section and displays each cross section plane as a semi-transparent 2D plane. However, in some embodiments, user interface 22 may display a single cross section plane or no cross section plane.

In any case, any rendered cross section planes are rendered based on the type of cross section selected by practitioner 8. User interface 22 provides an interface, such as a GUI, for receiving input from practitioner 8, e.g., via a keyboard, joystick, or a pointing device, for manipulating, i.e. rotating, tilting, and opening or closing, the virtual dental arch, thereby allowing practitioner 8 to view the virtual dental arch from various viewpoints.

GUI control module 24 provides user interface 22 as a graphical user interface (GUI) that allows practitioner 8 to the position of the cross section planes in user interface 22. For example, in one embodiment, GUI control module 24 displays a control image of a second dental arch and one or more moveable lines based on a selected type of cross section. In some embodiments, the control image comprises a plan view image of a generic dental arch that is orthogonal to the selected type of cross section. In other embodiments, the control image comprises a scaled plan view image of the virtual dental arch that is orthogonal to the selected type of cross section. In either case, the orientation of the control image is constant, i.e., the orientation of the control image does not change as practitioner 8 manipulates the virtual dental arch by interacting with user interface 22.

Accordingly, GUI control module 24 also provides an interface for receiving input from practitioner 8 to select the type of cross section and to select the position of the cross section controls, e.g., the parallel lines, relative to the control image. For example, GUI control module 24 may include a series of radio or graphical buttons that indicate the currently selected view by which practitioner selects the type of cross section to view in the 3D environment. Alternatively, GUI control module 24 may provide a menu-driven interface by which practitioner 8 selects the type of cross section.

In one embodiment, when practitioner 8 selects a frontal cross section, GUI control module 24 displays a front plan view image of a dental arch and two vertical moveable parallel lines that correspond to frontal cross section planes in the 3D environment. When practitioner 8 selects a sagittal cross section, GUI control module 24 displays a side plan view image of a dental arch and two vertical moveable parallel lines that correspond to sagittal cross section planes in the 3D environment. When practitioner 8 selects an occlusal cross section, GUI control module 24 displays a front plan view image of a dental arch and two horizontal moveable parallel lines that correspond to occlusal cross section planes in the 3D environment. In this manner, GUI control module 24 provides a clear indication of the type of cross section being shown regardless of the orientation of the patient's virtual dental arch within the 3D environment.

The interface may also receive input from practitioner 8 via a keyboard, joystick, or pointing device for selecting the position of the moveable parallel lines relative to the control image. In addition, the interface may receive input from practitioner 8 to adjust the orientation of the parallel lines. The two moveable parallel lines are relationally linked to the cross section planes within the 3D environment in that the positions or orientations of the parallel lines relative to the control image approximate the positions and orientations of the cross section planes relative to the patient's virtual dental arch displayed by user interface 22. Thus, by interacting with the interface provided by GUI control module 24 to select the position or orientation of the parallel lines relative to the control image, practitioner 8 can control the position or orientation of the cross section planes displayed within the interface provided by user interface 22.

Unlike conventional modeling software that provides a single display region for viewing a virtual dental arch and selecting a position of a cross section, user interface 22 and GUI control module 24 provide separate display regions, thereby allowing practitioner 8 to manipulate the view of the virtual dental arch of patient 6 within the 3D environment relatively independent from the control image for positioning of the cross section planes relative to the dental arch. As a result, GUI control module 24 may provide intuitive tools that allow practitioner 8 to easily select the position of cross section planes relative to the virtual dental arch while allowing practitioner 8 to view the changing cross section area of the virtual dental arch.

Modeling software 20 interacts with database 30 to access a variety of data, such as 3D data 32, and cross section data 36. Database 30 may be represented in a variety of forms including data storage files, lookup tables, or a database management system (DBMS) executing on one or more database servers. The database management system may be a relational (RDBMS), hierarchical (HDBMS), multidimensional (MDBMS), object oriented (ODBMS or OODBMS) or object relational (ORDBMS) database management system. The data may, for example, be stored within a single relational database such as SQL Server from Microsoft Corporation.

3D data 32 includes information defining 3D objects that represent each tooth and cross section plane within the 3D environment. Rendering engine 26 accesses and renders 3D data 32 to generate the virtual dental arch presented to practitioner 8 by user interface 22. The intersection of the cross section planes with the virtual dental arch defines one or more cross section areas. Rendering engine 26 accesses and renders 3D data 32 to generate the defined cross sections and, more particularly, the cross section areas of the virtual dental arch based on the position of the cross section planes. User interface 22 displays the virtual dental arch generated by rendering engine 26 to practitioner 8 and allows practitioner 8 to change viewing perspectives within the 3D environment.

Cross section data 36 specifies a variety of types of cross section planes that may be selectively positioned by practitioner 8 to assist in visualizing a cross section of the virtual dental arch. In one embodiment, user interface 22 may display any of frontal cross section planes, sagittal cross section planes, or lateral cross section planes in accordance with the type of cross section selected by practitioner 8. The cross section planes may be rendered parallel and equidistant from the corresponding mid-frontal, mid-sagittal, or mid-lateral cross section plane of the virtual dental arch, respectively.

In addition to defining the types of cross section planes, cross section data 36 stores attributes for the different types of cross section planes. Exemplary attributes include the current location and orientation of each of the cross section planes. As previously described, the location and orientation of the cross section controls (e.g., parallel lines) relative to the control image may be viewed as relationally linked to the position and orientation of the cross section planes relative to the patient's virtual dental arch. Thus, cross section data 36 may store data corresponding to the position of the cross section controls and data corresponding to the orientation of the parallel lines. GUI control module 24 updates these stored values in response to receiving input from practitioner 8 to select the position and orientation of the cross section controls relative to the control image displayed in the GUI.

Other attributes stored in cross section data 36 include defined initial locations, size of cross section planes and enablement of gridlines. For example, the cross section planes may initially be located on either side of the virtual dental arch based on the selected type of cross section. In this manner, practitioner 8 can visualize the entire virtual dental arch before positioning the cross section planes to selectively view a cross section of the virtual dental arch. The cross section planes may each be displayed as having a size larger than the virtual dental arch. Consequently, the cross section planes provide a good visual indication of the position of the cross section planes relative to the virtual dental arch. When enabled, the gridlines may be rendered at regular, discrete intervals, e.g., every millimeter, to allow visual measurements. For example, practitioner 8 may utilize the grid to visually measure the tooth.

Moreover, cross section data 36 may include a set of control images that are displayed by GUI control module 24 based on the type of cross section selected by practitioner 8. Thus, GUI control module 24 may access cross section data 36 to display the appropriate control image in response to practitioner 8 selecting a particular type of cross section.

Cross section control module 28 generally controls the location and orientation of the cross section planes based on cross section data 36 and, thus, also controls the viewable cross section(s) of the virtual dental arch. For example, cross section control module 28 automatically adjusts the location and orientation of the cross section planes relative to the virtual dental arch in response to GUI control module 24 receiving input from practitioner 8 to select the position and orientation of the parallel lines relative to the control image. As an example, when GUI control module 24 receives input from practitioner 8 to select the position and orientation of the parallel lines relative to the control image, GUI control module 24 may update the appropriate data stored in cross section data 36. Cross section control module 28 may then access cross section data 36 and process or convert the stored data to adjust the position and orientation of the cross section planes within the 3D environment. For example, cross section control module 28 may process the data using a simple algorithm to map the location of the cross section controls relative to a coordinate system associated with the dental arch of the control image to a coordinate system associated with the patient's dental arch. This process may execute in real-time so that it appears to practitioner 8 that the viewable cross section of the virtual dental arch within the 3D environment changes as practitioner 8 changes the position and orientation of the cross section controls relative to the control image within the GUI.

During this process, rendering engine 26 accesses 3D data 32 to generate the 3D representation of the virtual dental arch using 3D data 32. For example, in one embodiment, rendering engine 26 renders only the portion of the virtual dental arch located between the cross section planes. Rendering engine 26 may communicate with cross section control module 28 to provide the location and orientation of the cross section planes so that rendering engine only renders this portion.

Furthermore, GUI control module 24 may also automatically update user interface 22 in response to receiving input from practitioner 8 for selecting the position and orientation of the parallel lines relative to the control image. For example, GUI control module 24 may shade or hide a portion of the control image that is not located between the cross section controls, i.e., a "not-in-view" portion of the control image.

In some embodiments, GUI control module 24 may display a control image comprising a scaled plan view image of the virtual dental arch based on the selected type of cross section rather than a plan view image of a generic dental arch. In such embodiments, GUI control module 24 may be linked to 3D data 32 that defines the virtual dental arch, but the scaled plan view image does not change in orientation regardless of the orientation of the virtual dental arch within the 3D environment.

Figure 3:
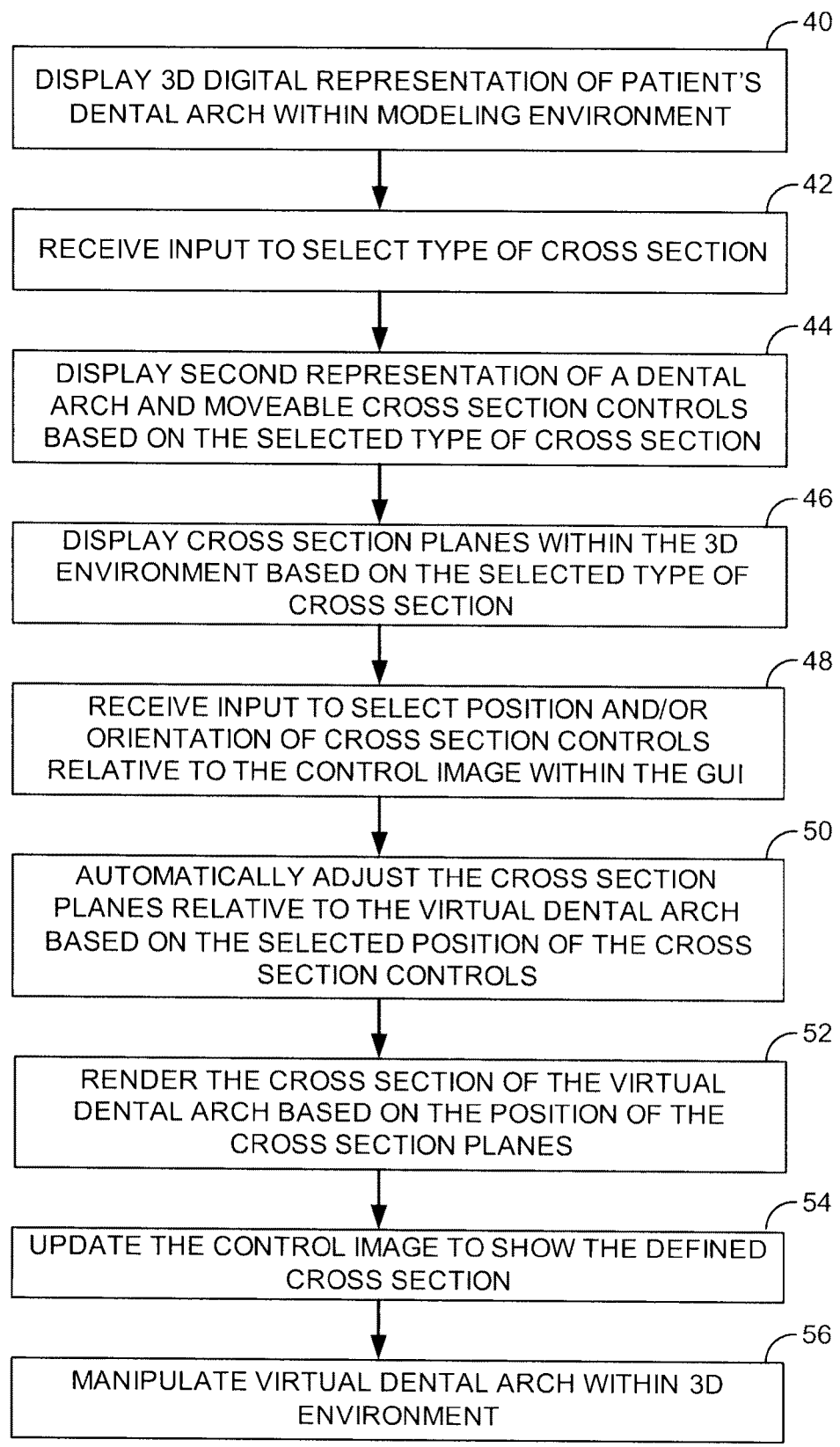
FIG. 3 is a flowchart illustrating exemplary operation of modeling software executing on the client computing device.

FIG. 3 is a flow chart illustrating an example operation of modeling software 20 executing on computing device 4. More specifically, the flowchart of FIG. 3 illustrates operation of modeling software 20 as a visual aid for selecting the position of cross section planes relative to the virtual dental arch while viewing a cross section of a virtual dental arch within the 3D environment.

Initially, modeling software 20 displays a 3D representation of a patient's dental arch, i.e., a virtual dental arch, within the modeling environment (40). As previously described, the virtual dental arch may be generated by digitally scanning a physical dental impression of the teeth of patient 6, scanning a physical casting made of the impression or by using an intraoral scanner to directly scan the teeth of patient 6. By interacting with controls associated with the 3D environment, practitioner 8 may view the virtual dental arch from various viewpoints, e.g., by rotating, tilting, or opening and closing, the virtual dental arch.

Next, modeling software 20 receives input to select the type of cross section from practitioner 8 (42) and, based on the input, displays a second representation (e.g., a control image) of a dental arch and one or more cross section controls (e.g., two moveable parallel lines) within the GUI (44). The GUI may include a set of radio buttons or graphical buttons with which practitioner 8 can interact to select the type of cross section. Alternatively, the GUI may provide a menu-driven interface by which practitioner 8 selects the type of cross section.

As previously described, the control image may comprise a plan view image of a generic dental arch, such as an icon or background image, or a scaled plan view image of the virtual dental arch. In either case, modeling software 20 may display the control image as a dental arch representation that is orthogonal to the selected type of cross section and display the cross section control as moveable parallel lines that correspond to the selected type of cross section. For example, when practitioner 8 selects a frontal cross section, the control image comprises a front plan view image and vertical moveable parallel lines. When practitioner 8 selects a sagittal cross section, the control image comprises a side plan view image and vertical moveable parallel lines. When practitioner 8 selects a lateral cross section, the control image comprises a frontal plan view image and horizontal moveable parallel lines. In some embodiments, modeling software 20 may display a pair of vertical or horizontal parallel lines. In other embodiments, modeling software 20 may display a single vertical or horizontal line.

Modeling software 20 also displays cross section planes within the 3D environment based on the input (46). Each cross section plane within the 3D environment corresponds to a vertical or horizontal line within the GUI. Thus, modeling software 20 displays a single cross section plane in embodiments in which a single vertical or horizontal line is displayed in the GUI and displays two cross section planes in embodiments in which a pair of parallel lines are displayed within the GUI. Because the cross section planes are relationally linked to the parallel lines, the cross section planes are displayed in a similar fashion as the parallel lines, i.e., frontal cross section planes are displayed when practitioner 8 selects a frontal cross section, sagittal cross section planes are displayed when practitioner 8 selects a sagittal cross section, and lateral cross section planes are displayed when practitioner 8 selects a lateral cross section. In particular, if the virtual dental arch is not currently displayed so that the cross section plane is parallel to the viewing plane of the computer screen, modeling software 20 may manipulate the virtual dental arch as such.

Each of the cross section planes may be displayed as a semi-transparent 2D plane. Because the cross section planes are semi-transparent, practitioner 8 can see the virtual dental arch through the cross section planes. In this manner, the cross section planes do not block practitioner 8 from viewing the virtual dental arch and may assist practitioner 8 in visually determining the distance between the cross section plane and other objects with the 3D environment, such as a surface of a tooth. In addition, the cross section planes may assist practitioner 8 in visualizing any portions of a tooth that may be penetrating the cross section plane. Moreover, the moveable parallel lines and cross section planes may initially be displayed outside of the control image and virtual dental arch, respectively.

Modeling software 20 may then receive input to select the position and/or orientation of the moveable cross section controls relative to the control image within the GUI (48). For example, practitioner 8 may select the position and/or orientation of the moveable parallel lines using a mouse, joystick, keyboard, or pointing device. Generally, practitioner 8 may select the position of each of the lines individually. In this manner, practitioner 8 can select the position of each cross section plane individually to limit the overall width of the cross section. When using a mouse, practitioner 8 may select the position of one of the moveable parallel lines by moving the cursor of the mouse over the line. When the cursor is positioned over the line, the cursor may change to a "grab" icon. By holding down the left button of the mouse while moving the mouse, practitioner 8 can move a horizontal line side-to-side or a vertical line up-and-down relative to the control image. In other embodiments, modeling software 20 may receive input from practitioner 8 to select the position of the cross section controls in the form of a menu-driven interface, keyboard commands, and graphical buttons or controls associated with the GUI, such as a slide bar or arrow buttons.

In a similar fashion, practitioner 8 may use a mouse to select the orientation of the cross section controls. For example, when practitioner 8 positions the cursor of a mouse over an endpoint of one of the parallel lines, the cursor may change to a rotation icon. By moving the mouse while holding down the left button of the mouse, practitioner 8 may select the orientation of the cross section controls, i.e., rotate or angle the cross section controls relative to the control image. Modeling software 20 may also receive input from practitioner 8 to select the position of the cross section controls in the form of a menu-driven interface, keyboard commands, and graphical buttons or controls associated with the GUI. Generally, the moveable parallel lines rotate as a group rather than individually. Thus, practitioner 8 may select the orientation of the moveable cross section controls by positioning the cursor of the mouse over any one of the end points of the moveable parallel lines. In some embodiments, however, practitioner 8 may select the orientation of each cross section control individually.

Once modeling software 20 automatically adjusts the cross section planes relative to the virtual dental arch within the 3D environment based on the selected position of the cross section controls relative to the control image (50), modeling software may then render the cross section of the virtual dental arch based on the position of the cross section planes (52). In addition, modeling software 20 updates the control image within the GUI to show the defined cross section (54). Updating the control image may comprise displaying the portion of the control image that is not located between (i.e., bounded by) the moveable cross section controls as a shaded out portion or not displaying this portion at all.

In some embodiments, modeling software 20 may execute steps 50, 52, and 54 substantially simultaneously so that it appears to practitioner 8 that the cross section of the control image and the virtual dental arch change as the position and/or orientation of the parallel lines change. In this manner, practitioner 8 can view the cross section area of the virtual dental arch while adjusting the position and/or orientation of the cross planes by interacting with the moveable cross section controls within the cross section tool. Because the position and orientation of the moveable cross section controls relative to the control image is used to define the position and orientation of the cross section planes relative to the virtual dental arch, the cross section controls and the control image act as a good visual aid for specifying a cross section of the virtual dental arch.

Finally, practitioner 8 may interact with modeling software 20 to manipulate the virtual dental arch within the 3D environment (56). In this manner, practitioner 8 may view the virtual dental arch from various viewpoints by interacting with the controls associated with the 3D environment. For example, practitioner 8 may rotate the virtual dental arch back and forth to compare opposite sides of the cross section without changing the view or display of the control image and the cross section controls. Consequently, modeling software 20 provides a separate portion of the GUI to aid selection of the position and orientation of cross section planes and, thus, enables practitioner 8 to view a cross section of the virtual dental arch while selecting the position of cross section planes that define the cross section.

Figure 4:
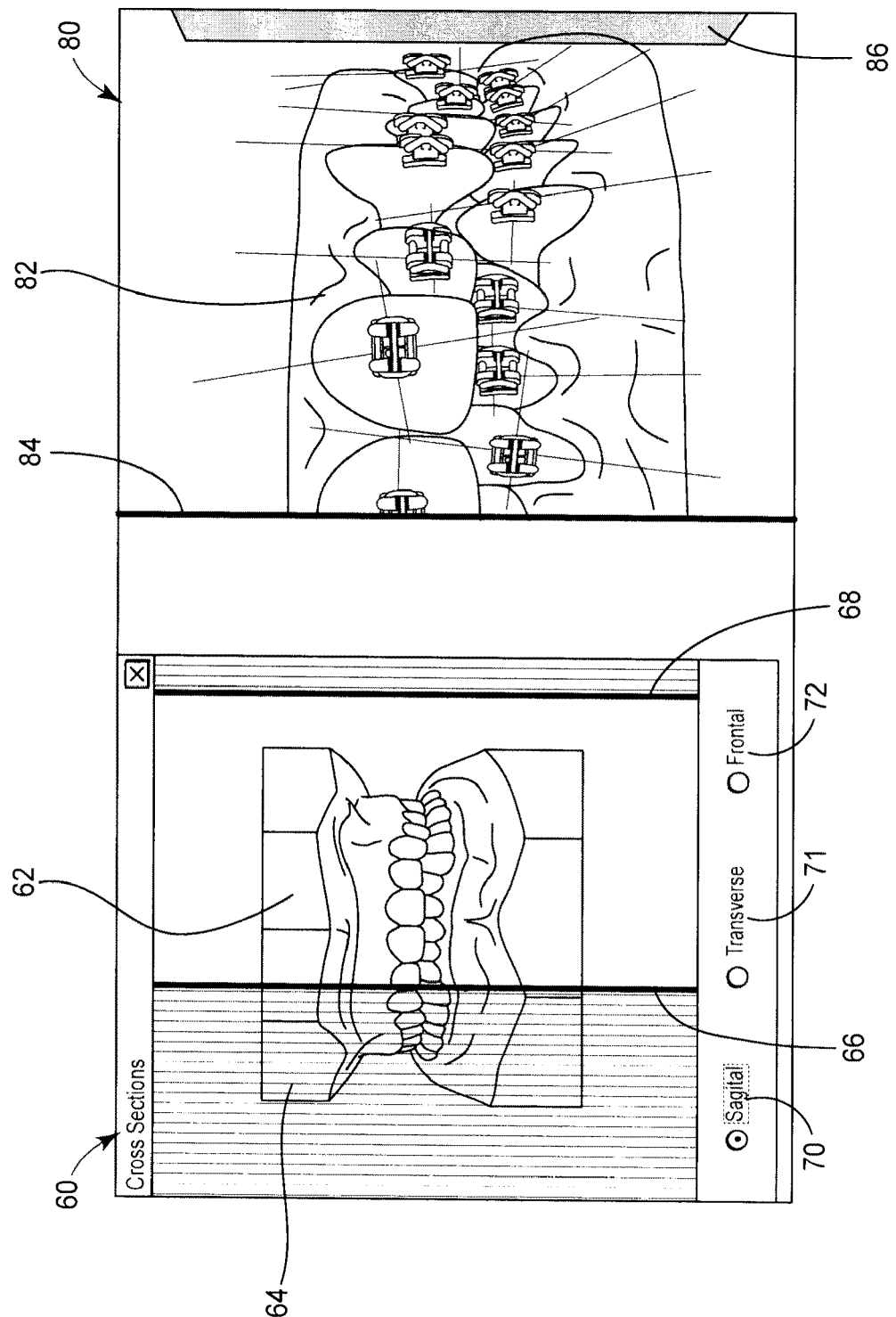
FIGS. 4-9 are display diagrams of an exemplary computer environment and GUIs presented by the modeling software.

FIGS. 4-9 are display diagrams illustrating an exemplary GUI presented by modeling software 20. For example, FIG. 4 illustrates an exemplary 3D environment 80 that includes a first region for displaying a virtual dental arch 82 and a separate display area 60 as a second region for specifying a cross section of virtual dental arch 82.

In the illustrated embodiment, cross section planes 84 and 86 are displayed within the first region as semi-transparent 2D planes and define the cross section area of virtual dental arch. Display area 60 includes a control image 62 that presents a representation of a second dental arch, and two moveable parallel lines 66 and 68 as cross section controls. Display area 60 also includes radio buttons 70, 71 and 72 for selecting the type of cross section as sagittal, lateral and frontal, respectively. In the illustrated embodiment, practitioner 8 has selected a sagittal cross section by activating radio button 70. As previously described, the position of moveable parallel lines 66 and 68 relative to control image 62 approximate the position of cross section planes 84 and 86 relative to virtual dental arch 82. In particular, because control image 62 displays a front plan view image of a generic dental arch, parallel lines 66 and 68 can be viewed as end on views of cross section planes 84 and 86. Accordingly, the position of parallel line 66 relative to control image 62 approximates the position of cross section plane 84 relative to virtual dental arch 82. In addition, display area 60 indicates that the portion of virtual dental arch corresponding to portion 64 of control image 62 is not-in-view by shading portion 64.

In general, FIG. 4 illustrates a configuration in which practitioner 8 cannot yet adequately view the cross section area of virtual dental arch 82 defined by the position of cross section planes 84 and 86 due to the orientation of virtual dental arch 82. In particular, virtual dental arch 82 is oriented so that cross section planes 84 and 86 are substantially perpendicular to the computer screen, thereby preventing practitioner 8 from yet viewing the cross section area of virtual dental arch. In this manner, rather than illustrating the useful features of the invention, FIG. 4 provides an example illustrating the limitations that may arise when a practitioner is not able to view the cross section area of the patient's virtual dental arch separate from selection and positioning of the cross section planes that define the cross section.

Figure 5:
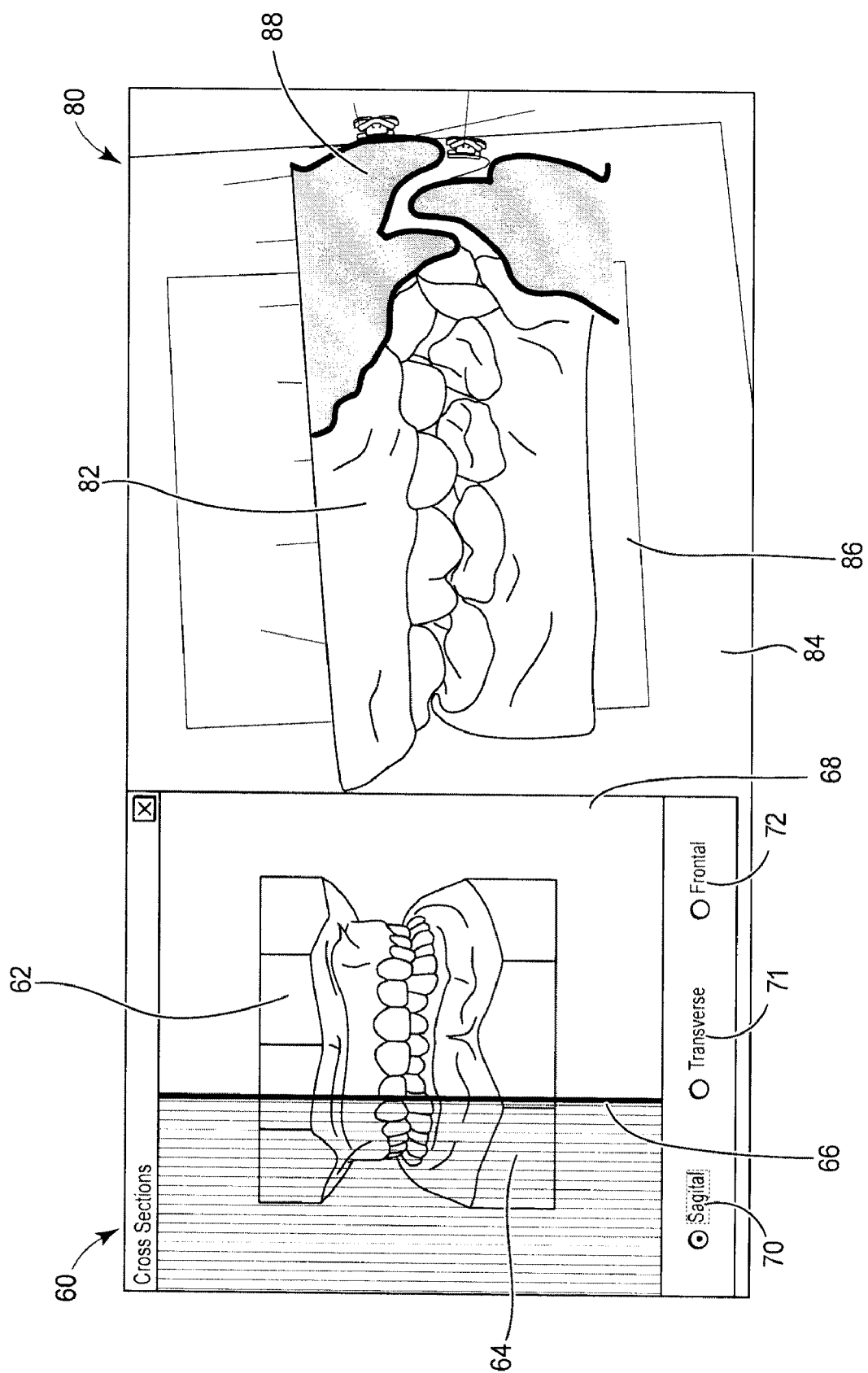

FIG. 5 illustrates an exemplary embodiment in which modeling software 20 displays virtual dental arch 82 within 3D environment 80 in a manner that allows practitioner 8 to view the cross section area 88 of virtual dental arch 82 while interacting with display area 60 to select the position of cross section planes 84 and 86. In the illustrated embodiment, practitioner 8 has manipulated virtual dental arch 82 and oriented the virtual dental arch so that cross section planes 84 and 86 are substantially parallel to the computer screen, thereby exposing the defined cross section. The orientation of control image 62 within display area 60 remains unchanged, allowing practitioner 8 to continue to manipulate parallel lines 66 and 68 to adjust cross section planes 84 and 86.

Figure 6:
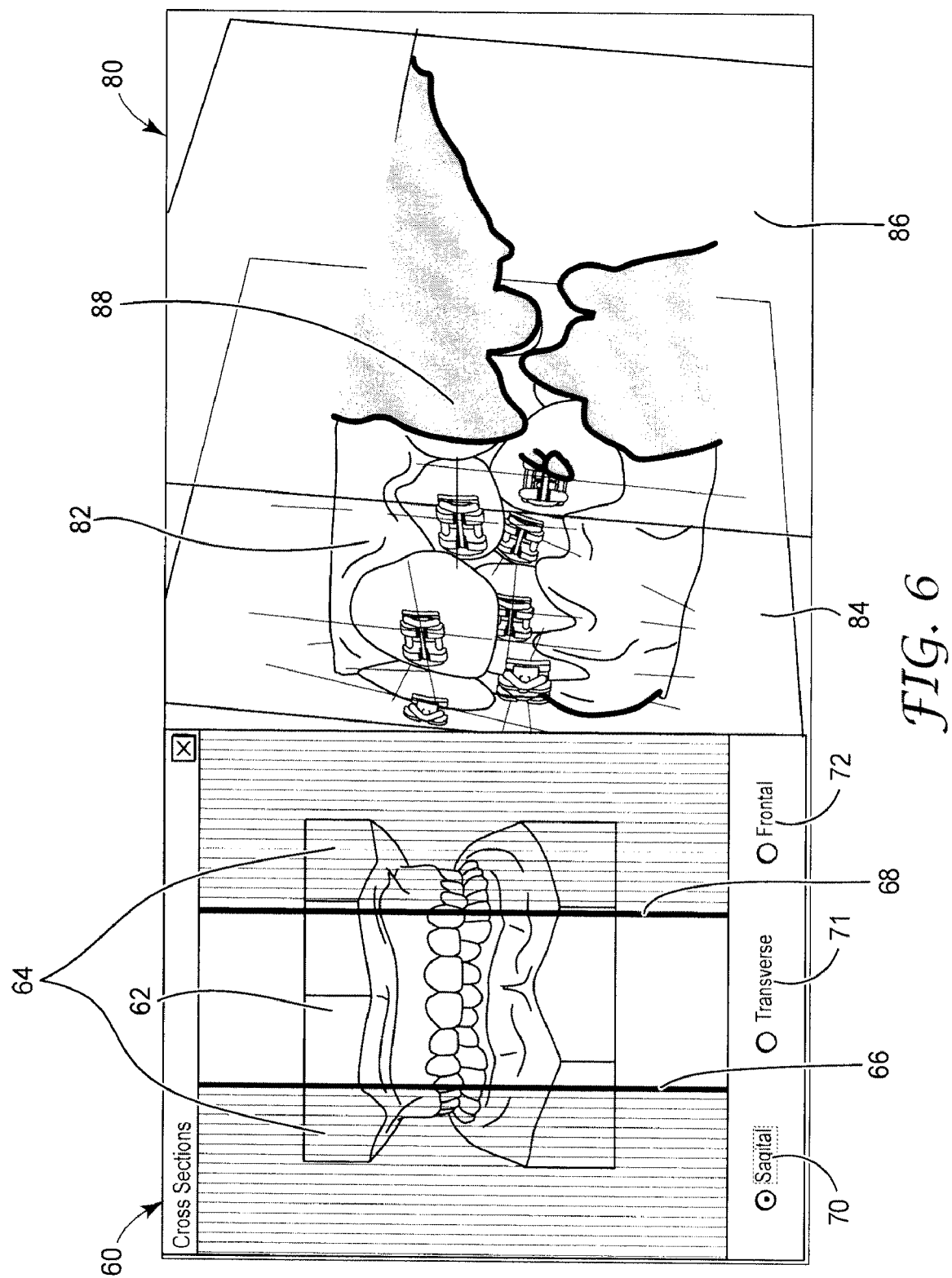

FIG. 6 illustrates an exemplary embodiment similar to FIG. 5, but in which parallel lines 66 and 68 are positioned to limit the overall width of control image 62 within display area 60. Accordingly, display area 60 displays both not-in-view portions 64 of control image 62 as shaded portions. Additionally, virtual dental arch 82 is oriented within 3D environment 80 such that cross section planes 84 and 86 are not substantially parallel to the computer screen, but still allow practitioner 8 to view cross section area 88 of virtual dental arch 82. In this manner, FIG. 6 illustrates the ability of modeling software 20 to allow practitioner 8 to view cross section area 88 of virtual dental arch 82 from various viewpoints by manipulating virtual dental arch within 3D environment 80 without altering the view of control image 62.

Figure 7:
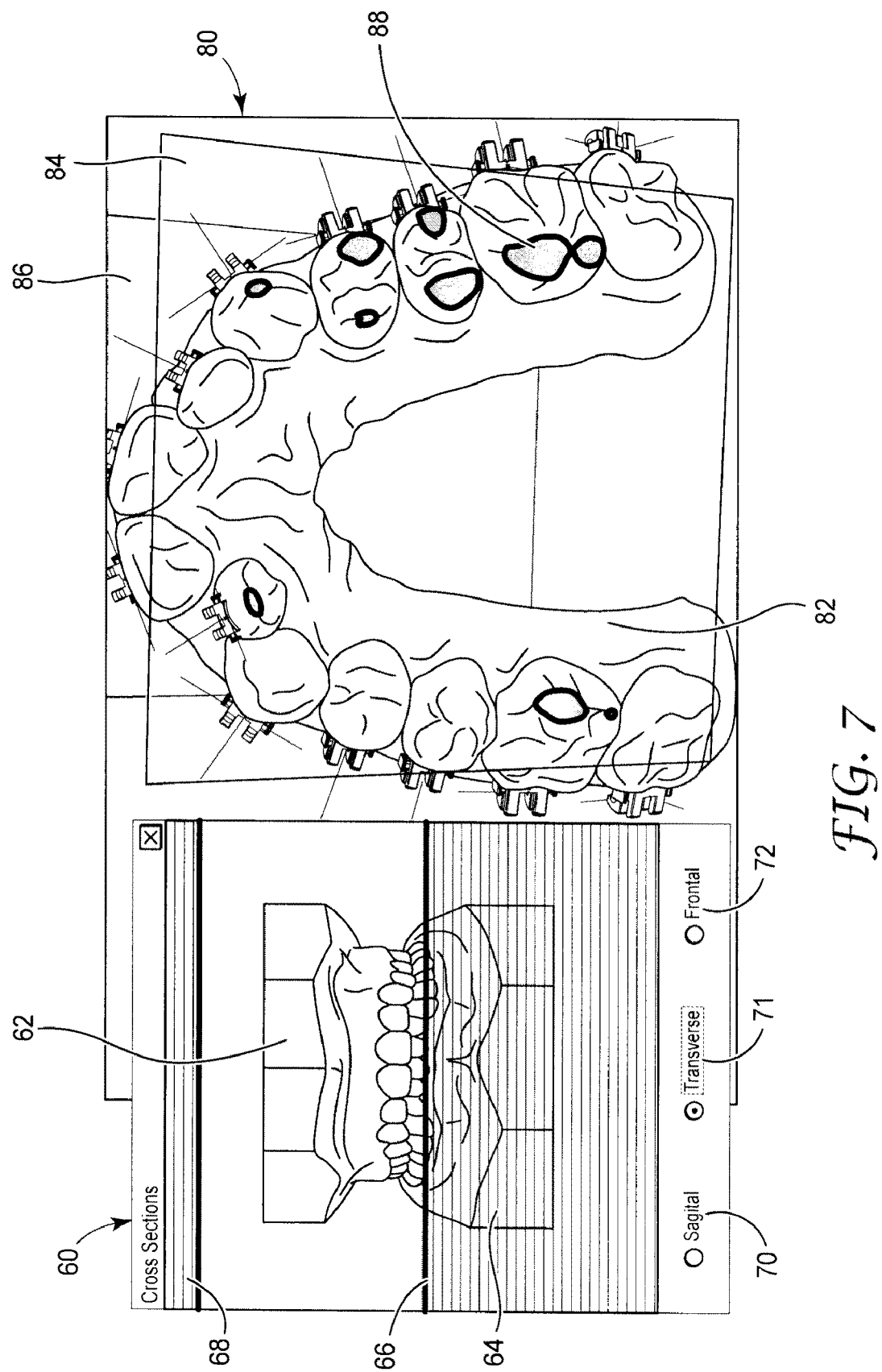

FIG. 7 illustrates an exemplary embodiment in which practitioner 8 selects an occlusal (lateral) cross section. In this mode, display area 60 renders control image 62 as a front plan view image of a generic dental arch (or scaled version of the patient's dental arch) and the cross section controls comprise two horizontal lines 66 and 68. The illustrated embodiment of FIG. 7 may be particularly useful to determine which lateral edge of virtual dental arch initially penetrates cross section plane 84. Practitioner 8 may determine which lateral edge initially penetrates cross section plane 84 by moving horizontal line 66 up-and-down relative to control image 62. Specifically, practitioner 8 may identify the initial lateral edge of virtual dental arch 82 to penetrate cross section plane 84 by moving horizontal line 66 towards the bottom of display area 60 from the illustrated position. The last cross section area 88 that is still visible is the lateral edge.

Figure 8:
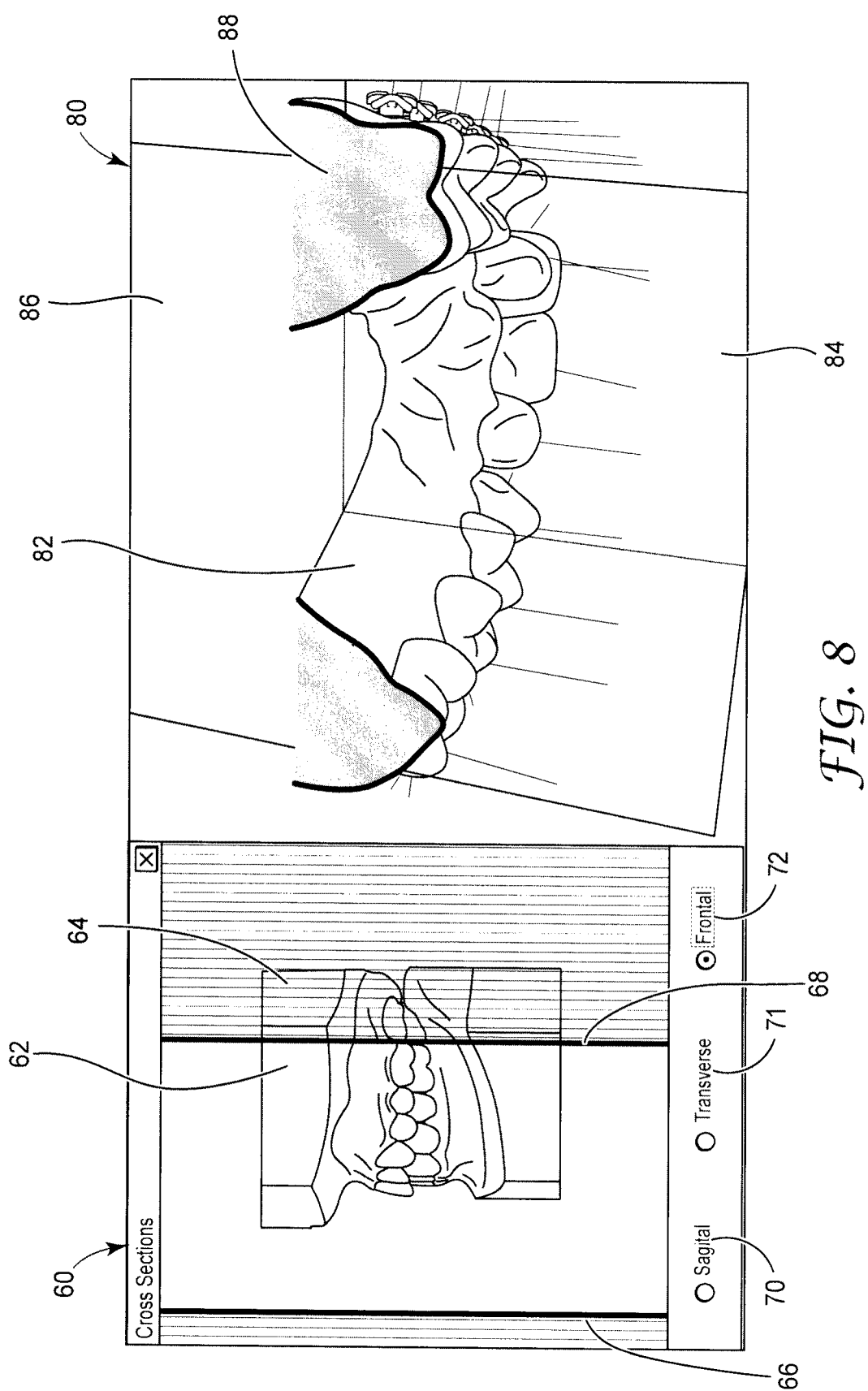

FIG. 8 illustrates an exemplary embodiment in which practitioner 8 selects a frontal cross section. In this embodiment, display area 60 displays control image 62 as a side plan view image of a generic dental arch (or scaled image) and displays cross section controls as two vertical parallel lines 66 and 68 relationally linked with cross section planes 84 and 86, respectively.

Figure 9:
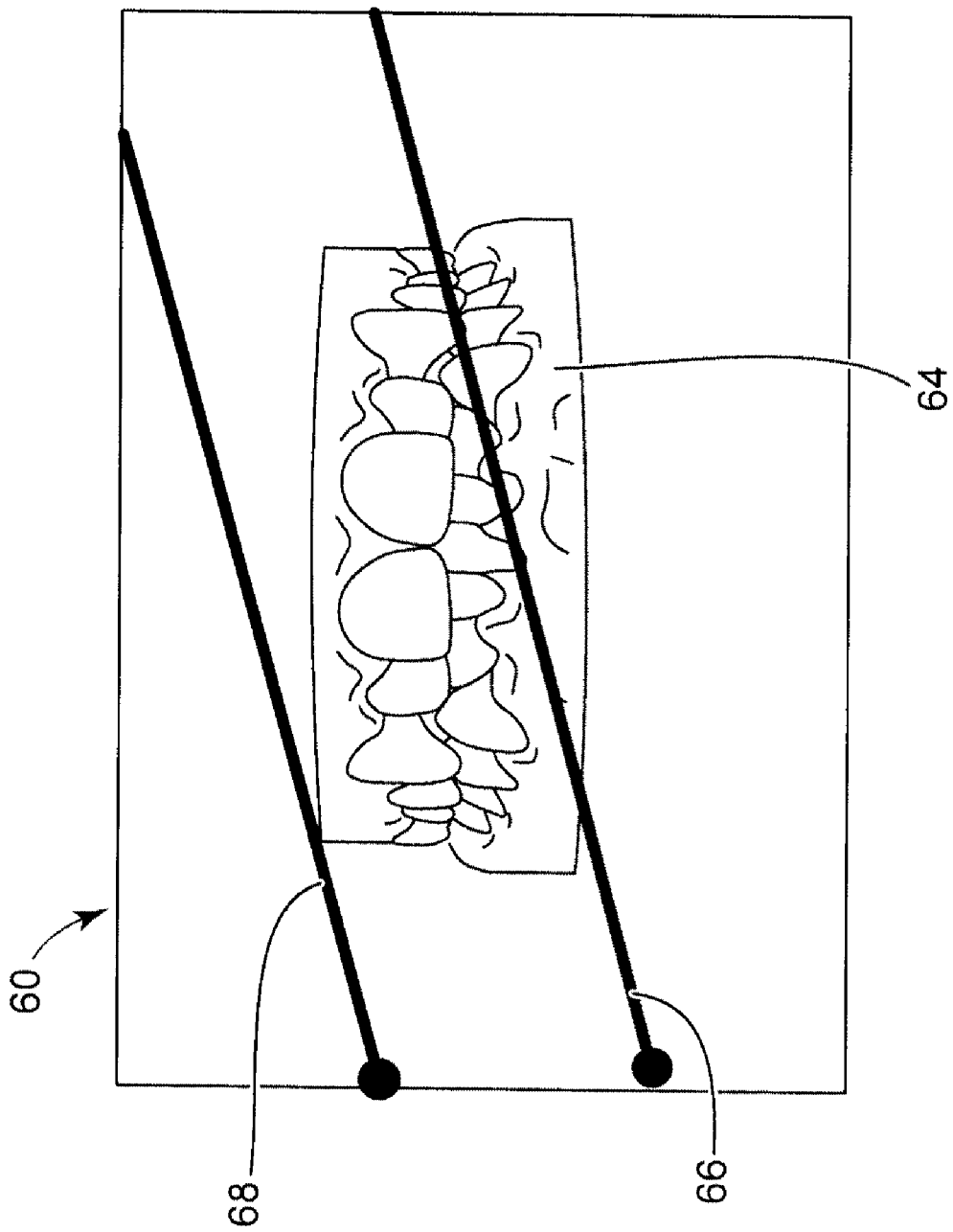

FIG. 9 illustrates another exemplary embodiment in which display area 60 allows practitioner 8 to rotate moveable parallel lines 66 and 68 to define angular cross sections through the patient's virtual dental arch.

Various embodiments of the invention have been described. Nevertheless, it is understood that various modifications can be made without departing from the invention. These and other embodiments are within the scope of the following claims.

The invention claimed is:

1. A method comprising:
displaying a graphical user interface (GUI) having a first region that includes a digital representation of at least a portion of a patient's dental arch within a three-dimensional (3D) environment and a second region that includes a digital representation of a second dental arch as a control image and at least one cross section control, wherein the cross section control is movable within the second region relative to the second dental arch to control a position of at least one cross section plane relative to the patient's dental arch within the first region, and wherein the cross section control comprises a moveable line within the second region, wherein the moveable line is positionable within the second region relative to the second dental arch based on input from a practitioner moving the moveable line in a horizontal direction relative to the second dental arch or moving the moveable line in a vertical direction relative to the second dental arch;

rendering a cross section of the patient's dental arch based on the selected position of the cross section plane;

in response to the input from the practitioner, automatically adjusting the position of the cross section plane within the 3D environment based on the position of the moveable line; and automatically updating the control image based on the selected position of the moveable line to provide an indication of a portion of the patient's dental arch that will not be rendered within the first region based on the position of the cross section plane.

2. The method of claim 1, further comprising:
receiving input from the practitioner that indicates a type of cross section; and
applying the cross sectional plane to the digital representation of the patient's dental arch and rendering the digital representation of the patient's dental arch based on the type of cross section indicated by the input.

3. The method of claim 1, wherein the type of cross section comprises one of a frontal cross section, a sagittal cross section or a lateral cross section.

4. The method of claim 1, further comprising determining the position of the cross section plane relative to the patient's dental arch based on a position of the moveable line relative to the control image.

5. The method of claim 1, wherein the control image comprises a plan view image of the second dental arch.

6. The method of claim 1, wherein the input from the practitioner indicates at least one of a position and an orientation of the moveable line.

7. The method of claim 1, further comprising rotating the moveable line relative to the control image in response to the input from the practitioner.

8. The method of claim 1,
wherein the type of cross section comprises a frontal cross section and the cross section plane comprise a frontal cross section plane, and
wherein displaying the control image comprises displaying a side plan view image of the second dental arch.

9. The method of claim 1,
wherein the type of cross section comprises a sagittal cross section and the cross section plane comprise a sagittal cross section plane, and
wherein displaying the control image comprises displaying a front plan view image of the second dental arch.

10. The method of claim 1,
wherein the type of cross section comprises a lateral cross section and the cross section plane comprise a lateral cross section plane, and
wherein displaying the control image comprises displaying a front plan view image of the second dental arch.

11. The method of claim 1, wherein the second dental arch comprises an image of a generic dental arch.

12. The method of claim 1, wherein the second dental arch comprises a low resolution version of the digital representation of the patient's dental arch.

13. The method of claim 1, wherein automatically updating the control image comprises rendering a portion of the second dental arch as a shaded portion to provide an indication of a portion of the patient's dental arch that will not be rendered within the first region based on the position of cross section plane.

14. The method of claim 1, wherein automatically updating the control image comprises blanking a portion of the second dental arch to provide an indication of a portion of the patient's dental arch that will not be rendered within the first region based on the position of cross section plane.

15. The method of claim 1, further comprising rendering the cross section plane within the first region as semi-transparent two-dimensional (2D) plane based on the position.

16. The method of claim 1, wherein rendering the digital representation of the patient's dental arch comprises rending the digital representation based on stored data and the selected position of the cross section plane.

17. The method of claim 1, wherein rendering the digital representation of the patient's dental arch comprises rendering a digital cross section of the patient's dental arch defined by the position of the cross section plane.

18. The method of claim 1, further comprising:

receiving input from the practitioner to manipulate the digital representation of the patient's dental arch within the 3D environment; and modifying the display of the patient's dental arch within the first region in response to the input without modifying the display of the second dental arch.

* * * * *